(12) United States Patent
Gravel et al.

(10) Patent No.: US 6,192,891 B1
(45) Date of Patent: *Feb. 27, 2001

(54) INTEGRATED SYSTEM INCLUDING MEDICATION DELIVERY PEN, BLOOD MONITORING DEVICE, AND LANCER

(75) Inventors: Marian Gravel, Newburgh, NY (US); Benjamin Gasparello, Quakertown, PA (US); Joseph Ferraro, Robbinsville, NJ (US); Ashutosh Sharma, Springfield, NJ (US); Robert John Strowe, Ramsey, NJ (US); Antonio A. Bendek, Vernon, NJ (US); Robert C. Uschold, Monroe, NY (US); William Thomas Antoshkiw, Wayne, NJ (US)

(73) Assignee: Becton Dickinson and Company, Franklin Lakes, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/299,410

(22) Filed: Apr. 26, 1999

(51) Int. Cl.$^7$ ............................. A61B 10/00; G06F 17/00
(52) U.S. Cl. ............................................. 128/920; 604/187
(58) Field of Search ........................... 604/207–211, 131, 604/151, 152, 187; 606/347, 365; D24/186; 600/300; 436/95; 128/920

(56) References Cited

U.S. PATENT DOCUMENTS 5,593,390 * 1/1997 Castellano et al. .................. 604/187

* cited by examiner

*Primary Examiner*—Sharon Kennedy
*Assistant Examiner*—Catherine Serke
(74) *Attorney, Agent, or Firm*—Alan W. Fiedler, Esq.

(57) ABSTRACT

A portable diagnostic and medication delivery system that includes a housing and a monitor disposed in the housing for monitoring a characteristic of a bodily fluid sample obtained from an individual. A medication delivery pen and a lancer are each removably mounted to the housing. The monitor, which may be integrated into the housing, may monitor blood glucose levels, for example, and the pen may be employed for the delivery of insulin.

45 Claims, 7 Drawing Sheets

INTEGRATED SYSTEM INCLUDING MEDICATION DELIVERY PEN, BLOOD MONITORING DEVICE, AND LANCER

BACKGROUND OF THE INVENTION

1. Field of the Invention

The subject invention relates to a diagnostic and medication delivery system having a medication delivery pen, blood monitoring device and a lancer removably mounted in a common housing.

2. Description of Related Art

Home diabetes therapy requires the patient to carry out a prescribed regimen that involves self-testing blood glucose levels and administering an appropriate dose of insulin. Insulin has traditionally been injected by a hypodermic syringe, which suffers from numerous drawbacks. For example, syringes are not preloaded with medication, requiring the user to carry a separate medical vial. Syringes also require a degree of dexterity and sufficient visual acuity on the part of the patient to line up the needle of the syringe with the rubber septum on the medical vial and to ensure that the syringe is loaded with the proper dosage. As a result, unintentional needle pricks commonly occur.

To overcome the drawbacks of syringes, medication delivery pens have been developed, which facilitate the self-administration of medication such as insulin. Such delivery pens use prepackaged insulin and may be used repeatedly until the medication is exhausted. Mechanical and electronic pens are available to the patient. Electronic pens incorporate electronic circuitry that sets and/or indicates the appropriate dosage of insulin and stores data for subsequent downloading such as the time, date, amount of medication injected, etc.

Glucose levels are monitored at periodic intervals to determine when another insulin injection should be taken or to determine how the user is responding to prior injections. The patient monitors blood levels by lancing a portion of the body with a lancer to take a blood sample. The blood sample is placed on a test strip that contains appropriate reagents for creating the chemical reactions necessary to measure glucose levels, which is subsequently analyzed by the blood glucose monitor. Typically, the patient then manually records the results, the time and date in a log book. To monitor glucose levels the patient is required to have available a lancer, test strips and a blood glucose monitor.

The self-treatment of diabetes therefore requires the patient to carry at least three devices: a medication delivery pen, a blood glucose monitor, and a lancer, as well as ancillary items such as test strips, lancets and needles. This can be inconvenient, cumbersome to use, etc.

A number of patents disclose systems that attempt to allow a patient to more conveniently perform the requisite procedures for treating diabetes. More particularly, U.S. Pat. No. 5,279,294 to Anderson et al. ("Anderson") discloses a portable unit that includes a glucose monitor and a lancer. The monitor and lancer are integrated in the housing. The lancer is not an independent component operably distinct from the housing. Rather, the housing includes a spring-actuated hammer for driving a disposable lancet. Since the lancer is integrated with the housing, it cannot be removed and used separately from the housing. U.S. Pat. No. 5,536,249 to Castellano et al. ("Castellano") discloses a medication delivery pen that is integrated with a blood glucose monitor. The pen and monitor are not independent units and thus cannot be used separately from one another.

While the above described systems facilitate the self-administration and monitoring of medication, there is a need for additional features and improvements for such systems. For example, neither of the known systems provide a single unit that integrates all the primary components (i.e., medication delivery pen, blood monitor and lancer) necessary to administer medication and monitor blood glucose levels. Moreover, these systems can be cumbersome to use because the components are not fully detachable from one another and thus each component cannot be used separately from the others at the appropriate point in the treatment process.

SUMMARY OF THE INVENTION

The subject invention relates to a portable diagnostic and medication delivery system that includes a housing and a monitor disposed in the housing for monitoring a characteristic of a bodily fluid sample obtained from an individual. A medication delivery pen and a lancer are each removably mounted to the housing. The monitor, which may be integrated into the housing, may monitor blood glucose levels, for example, and the pen may be employed for the delivery of insulin.

In accordance with one aspect of the invention, the housing has a first compartment adapted to receive and store the medication delivery pen and a second compartment adapted to receive and store the lancer. The first and second compartments may be integrally formed with and embedded in the housing.

In accordance with another aspect of the invention, a data port is located on the housing for downloading the characteristics of the bodily fluid. In those cases where an electronic medication delivery pen is employed, the data port may also receive and download information from the pen. Alternatively, a second data port may be used to download the information from the pen.

In accordance with another aspect of the invention, the monitor includes a display located on an inner surface of the second compartment so that the monitor is protected when the lancer is stored in the second compartment.

In accordance with yet another aspect of the invention, the housing further includes a third compartment adapted to store ancillary items such as test strips, lancets, and needles.

In accordance with another aspect of the invention, the first and second compartments include portions that extend internal to the housing for receiving and protecting a needle of the medication delivery pen and a lancet of the lancer, respectively.

In accordance with still another aspect of the invention, a diagnostic and medication delivery system is provided which includes a housing that has a first compartment adapted to receive and store a medication delivery pen and a second compartment adapted to receive and store a lancer. A monitor is integrated in the housing for monitoring a characteristic of a sample of a bodily fluid.

DETAILED DESCRIPTION

Figure 1:
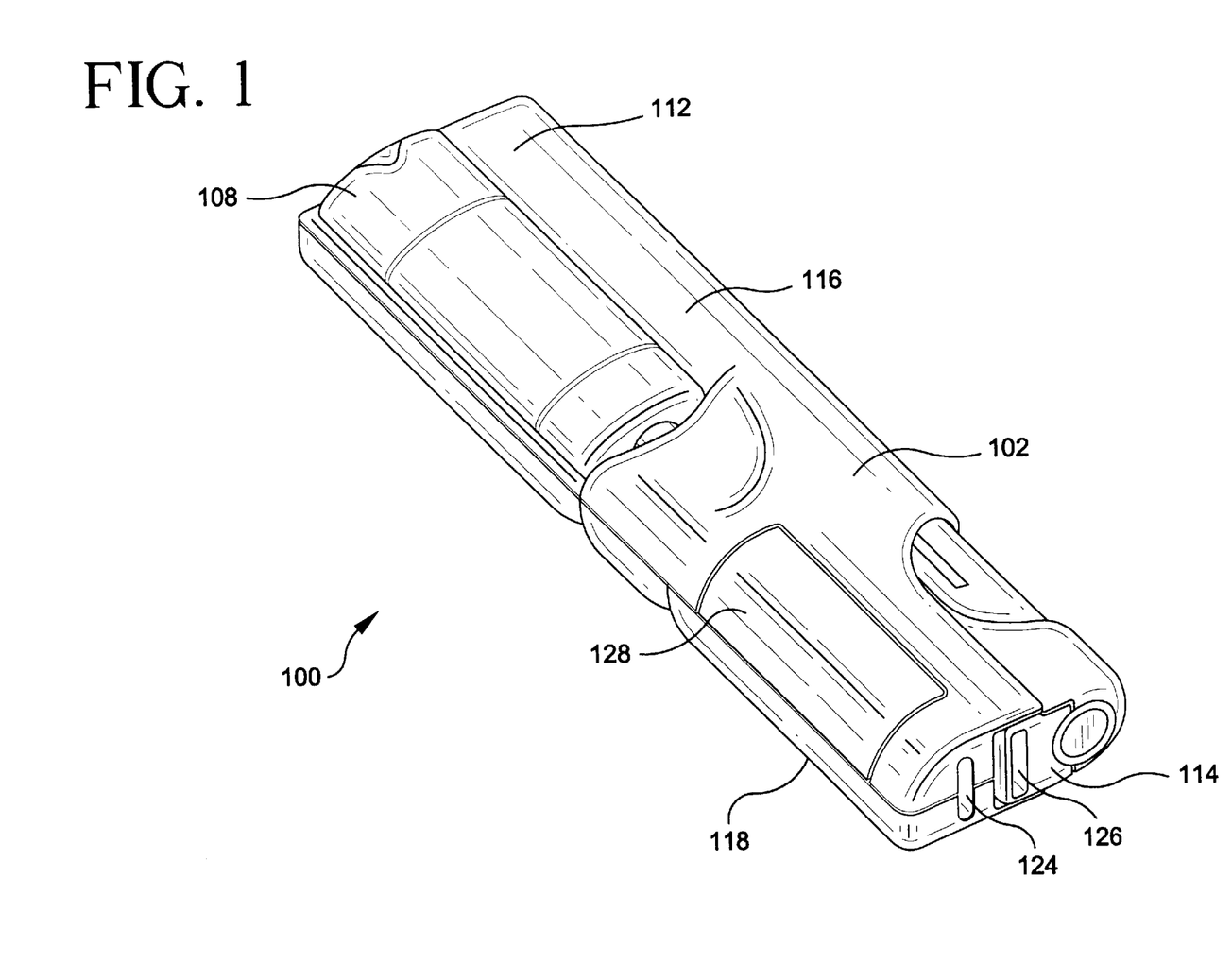
FIG. 1 is a perspective view of an integrated system for delivering medication and monitoring blood levels constructed in accordance with the present invention.
Figure 2:
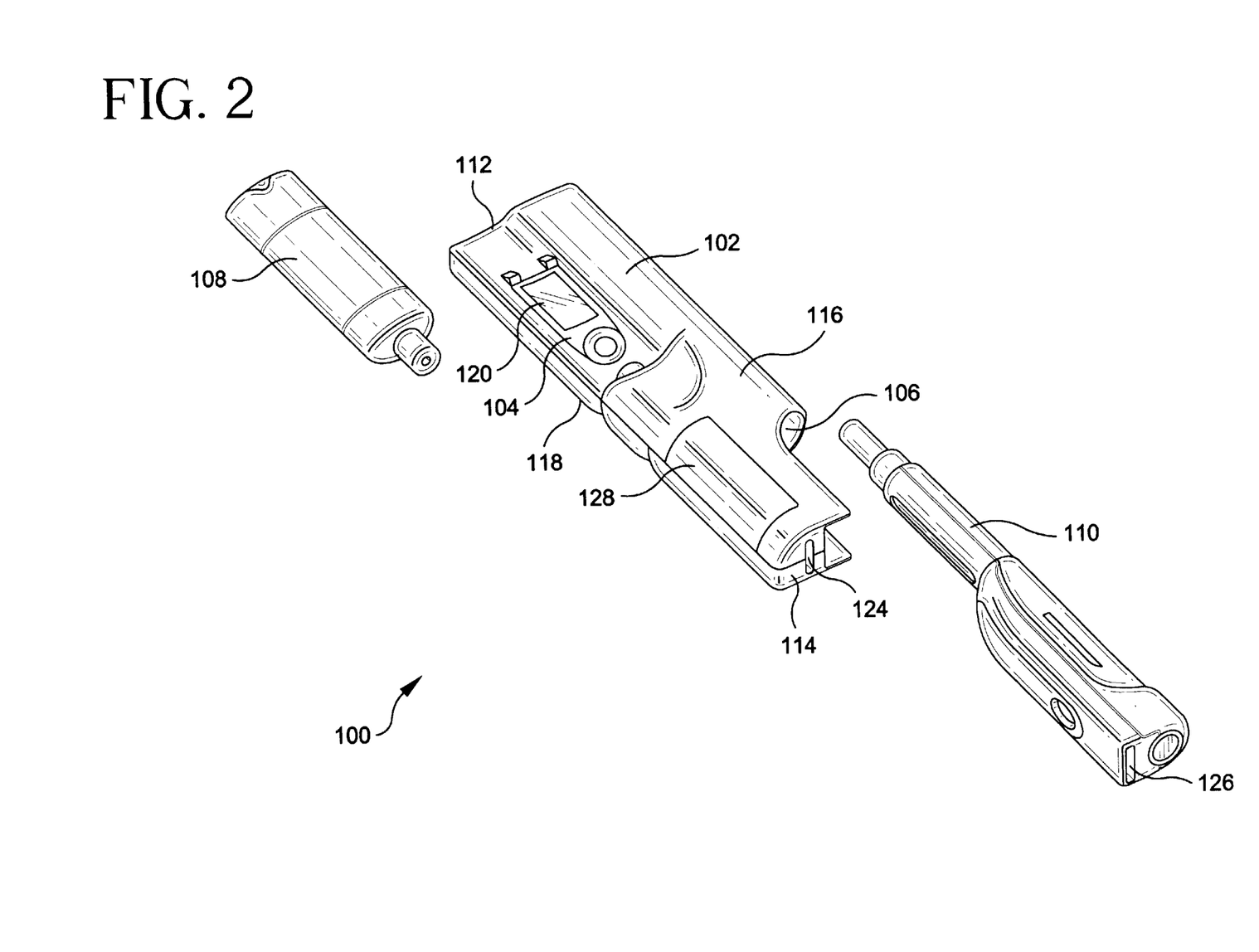
FIGS. 2 and 3 are perspective views of the integrated system shown in FIG. 1 with the medication delivery pen and lancer removed from their compartments.
Figure 3:
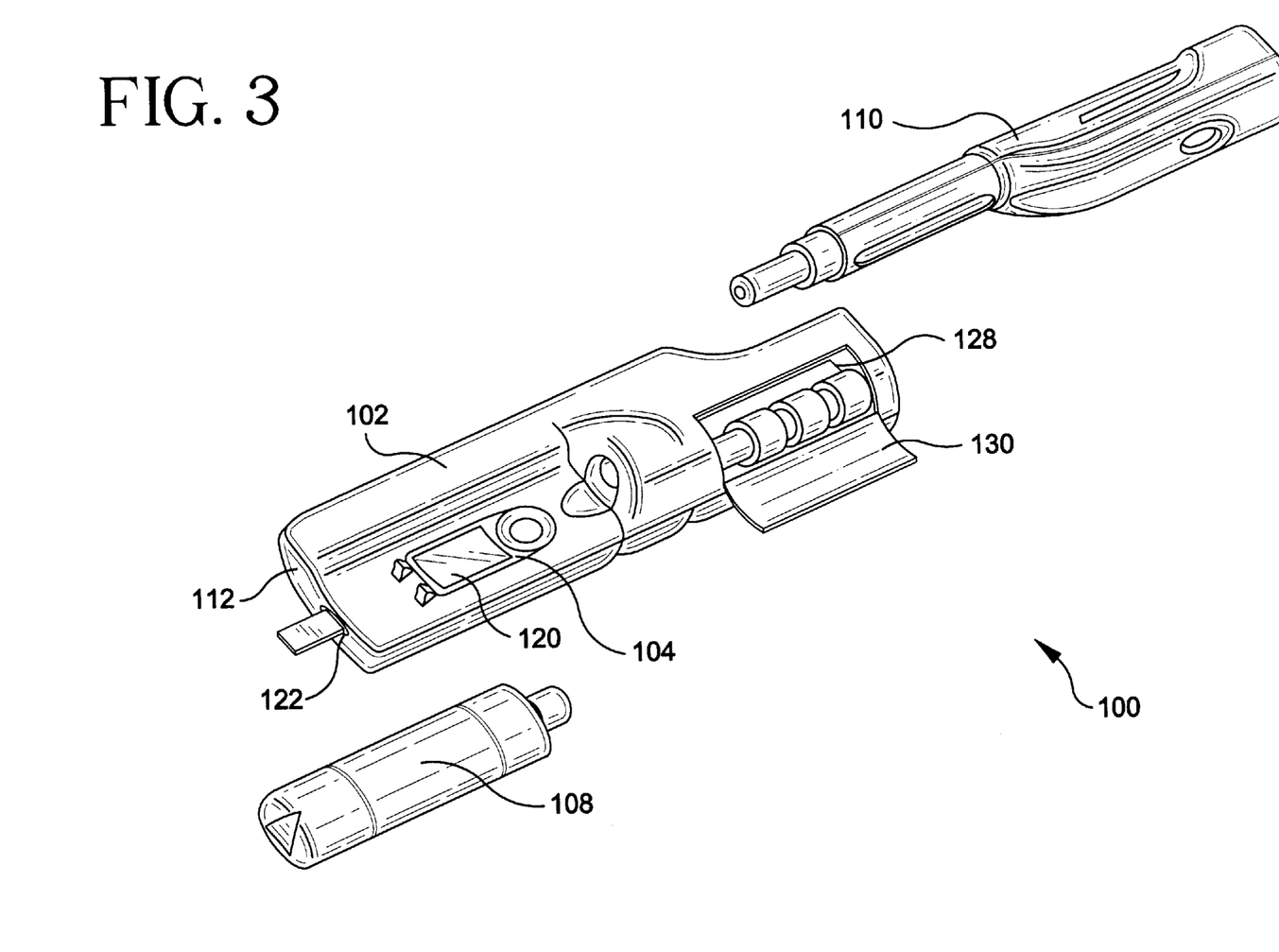

FIGS. 1–3 shows an exemplary embodiment of a diagnostic and medication delivery system 100 constructed in accordance with the present invention. The system 100 conveniently integrates a medication delivery pen, blood glucose monitor, and lancer into a single portable unit. The system 100 includes a housing 102 having a length defined by first and second end portions 112 and 114 and a thickness defined by opposing upper and lower surfaces 116 and 118. The housing 102 may have an overall rectangular footprint and the upper and lower surfaces 116 and 118 may be planar or, alternatively, may have either concave or convex curvatures. The curvatures of the upper and lower surfaces 116 and 118 need not match one another. In general, the housing 102 should have a configuration that allows it to be easily grasped and manipulated and thus is not limited to the shape shown in FIG. 1. The housing may be conveniently formed from two shells fastened together to form an enclosure in which the various components discussed below may be located.

The housing 102 provides mounting locations for a medication delivery pen, lancer, and glucose monitoring meter. Specifically, a lancer compartment 104 and pen compartment 106 are integrally formed with and embedded in the housing 102. The lancer compartment 104 is configured to receive a lancer 108 so that the lancer engages and slides in the lancer compartment in a manner that allows it to be easily inserted and removed. Likewise, the pen compartment 106 is configured to receive a medication delivery pen 110. When inserted in their respective compartments, a portion of the body of the lancer and pen are exposed so that they are readily accessible to the user. However, the compartments each include portions that extend internal to the housing 102 in which the lancet of the lancer and the needle of the pen are to be situated. Accordingly, the lancet and needle are protected by the housing 102 from environmental contamination. Thus, housing 102 provides protection to the needle of the pen, eliminating the need for a separate pen cap. Typically when not in use, a conventional lancer is stored with an open port or cover that exposes the lancet to the environment for possible contamination. However, when packaged in housing 102 of the present invention, the lancing port is completely covered providing protection from the environment to the lancet.

The medication delivery pen 110 may be of any type known to those of ordinary skill in the art. In general, the pen has a drive mechanism for accurate dosing and ease of use. A dosage mechanism such as a rotatable knob allows the user to accurately adjust the amount of medication that will be injected by the pen from a prepackaged vial of medication. To inject the dose of medication, the user inserts the needle under the skin and depresses the knob once as far as it will depress. The pen may be an entirely mechanical device or it may be combined with electronic circuitry to accurately set and/or indicate the dosage of medication that is injected into the user. The electronic circuitry may also serve to record data such as the date, time, amount of medication injected, etc. The data can be displayed on a display located on the pen. The display may be a mechanical display or an electronic display, depending on whether the pen is a mechanical or electronic pen. The information can also be downloaded via a data port 126 to a computer or other electronic storage device so that it may be subsequently reviewed by the user or a health professional. Likewise, data may be uploaded to the pen via data port 126 to install, for example, updated software. Examples of medication delivery pens that may be employed in the present invention are disclosed in U.S. Pat. Nos. 5,536,249, 5,827,232 and 5,582,598.

Similar to the medication delivery pen 110, the lancer 108 may be of any type known to those of ordinary skill in the art. The lancer 108 will typically include an actuator such as a button for actuating a mechanism that displaces a disposable lancet. The mechanism also returns the lancet to its initial position after it has been inserted into the finger of the user.

A glucose monitor is integrated into housing 102. The glucose monitor includes a display 120, a reaction chamber (not shown) disposed in the housing 102, and a test strip interface 122. The test strip interface 122 is located on the first end 112 of the housing 102 proximate the lancer compartment 104. A disposable test strip on which a blood sample is placed is inserted into the test strip interface 122. When a blood sample enters into the reaction chamber, the blood glucose level is measured using well-known electrochemical or reflectance techniques. In some embodiments of the invention electrochemical techniques are preferred because they require a relatively small sample of blood, employ a small test strip, and provide a quick response.

Electronics such as a microprocessor and other components, e.g., batteries, associated with the glucose monitor are located in the enclosure of housing 102. The electronic circuitry determines and stores the blood glucose level analyzed in the reaction chamber. A bidirectional data port 124 located on the housing 102 is coupled to the electronic circuitry for transferring data to or from an external device such as a computer, phone jack or a communication network. It should be noted that in some embodiments of the invention employing an electronic medication delivery pen having downloading capabilities, data ports 124 and 126 may be combined so that only a single port is required on housing 102. Moreover, aside from the data ports, the electronic pen and glucose monitor also may be in communication with one another both to share data and eliminate redundant components. For example, a single display may be provided on the housing for displaying the data from both the glucose monitor and the electronic pen. Furthermore, some embodiments of the invention may even employ a third display that integrates and displays the data from both the electronic pen and the glucose monitor.

In those embodiments of the invention that employ a mechanical delivery pen, the display located on the housing may be configured so that it automatically switches between two modes. In the first mode, when the pen is installed in the compartment 106 the display displays the blood glucose data. When the pen is removed from its compartment, the display switches to a mode that allows information from the medication delivery pen to be manually entered. This allows the patient to use the invention as a simple electronic log book to recall data from memory. Specifically, the user can enter the number of insulin units that are injected so that this data is stored in the electronics associated with the glucose monitor for subsequent downloading. This arrangement eliminates the need for manually recording the insulin dosage, which would otherwise be required with a mechanical pen. After the pen has been reinstalled in its compartment, the display automatically returns to displaying glucose levels.

In the particular embodiment of the invention shown in FIGS. 1–3, the display 120 of the glucose monitor is located in the lancer compartment 104 and forms a portion of the inner surface defining lancer compartment 104. Accordingly, the display 120 is only accessible when the lancer 108 has been removed from the lancer compartment 104 and is therefore protected when the lancer 108 is in place.

The housing 102 may optionally include an accessory compartment 128 for storing such ancillary items as test strips, lancets, and needles. The test strips may be housed in a container that itself is stored in the accessory compartment 128. In contrast to pen and lancer compartments 106 and 104, accessory compartment 128 includes a cover 130 that may be snapped or pivotally mounted to the housing 102. When closed, the cover 130 is flush with the surface of the housing 102. A desiccant may also be provided in accessory compartment 128 to enhance the useful lifetime of the test strips. In some embodiments of the invention the accessory compartment may be partitioned into two or more portions. One portion of the compartment can store unused items while another partition can be used to store used items such as used test strips until they can be otherwise disposed of.

The particular arrangement of components in the housing 102 which is depicted in the embodiment of the invention shown in the FIGS. allows the system to be used in a convenient fashion while reducing the likelihood that any of the components will be used improperly or in an improper sequence. For example, the pen and lancer compartments 106 and 104 are located on opposing ends of the housing to ensure an even distribution of weight along the housing and also to reduce the chance that the user will inadvertently interchange the medication delivery pen 110 and the lancer 108. In addition, the display 120 of the blood glucose monitor is located in the lancer compartment 104 so that it is only exposed when it is needed, e.g., immediately after blood has been drawn by the lancer 108. Likewise, the test strip interface 122 is located on the same end of the housing as the lancer compartment 104 since both will be used when monitoring blood glucose levels. Furthermore, the pen, lancer and accessory compartments 106, 104, and 128 may all be located on the same surface, e.g., upper surface 116, of housing 102. Of course, the present invention is not limited to the arrangement of the components shown in the FIGS. Rather, the invention contemplates that the components may be arranged in a variety of different configurations. For example, in some embodiments of the invention the pen and lancer compartments may be located on the same end of the housing rather than on opposite ends. Similarly, the display 120 of the glucose monitor need not be located in the lancer compartment but may be placed on any portion of the housing 102.

The present invention provides a number of important advantages over the previously mentioned systems. For example, in contrast to the known systems, the present invention integrates a medication delivery pen, blood glucose monitor, and lancer into a single unit containing everything necessary to inject insulin and monitor blood glucose levels while storing data that performs the functionality of a separate log book. Moreover, the pen and lancer are fully detachable from the remainder of the unit so that they may be used (or replaced in case of failure) independently of one another. Accordingly, the present invention offers the advantages of a fully integrated arrangement while additionally offering the advantages of an individual pen and lancer.

Figure 4:
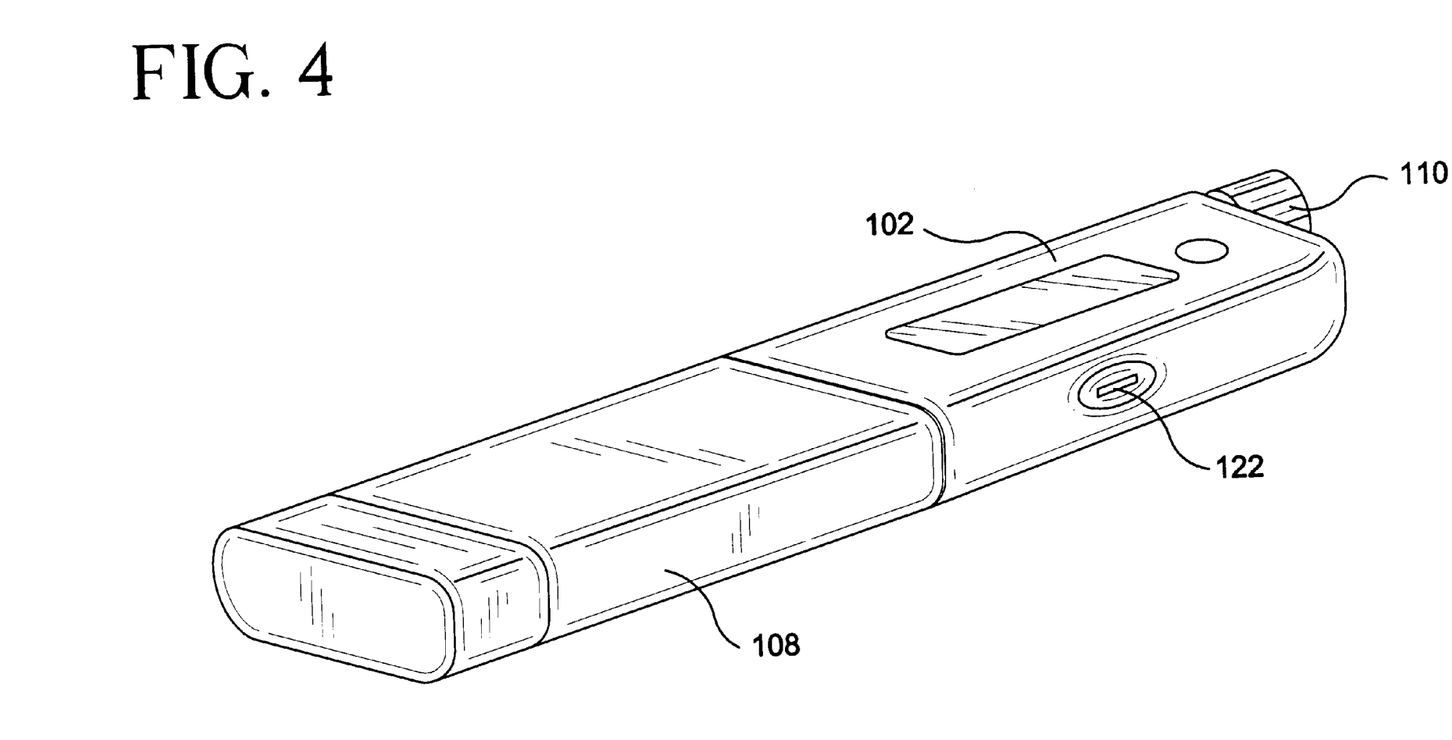
FIG. 4 shows an alternative embodiment of the invention in which the medical delivery pen and the blood glucose meter are integrated into a single housing.
Figure 5:
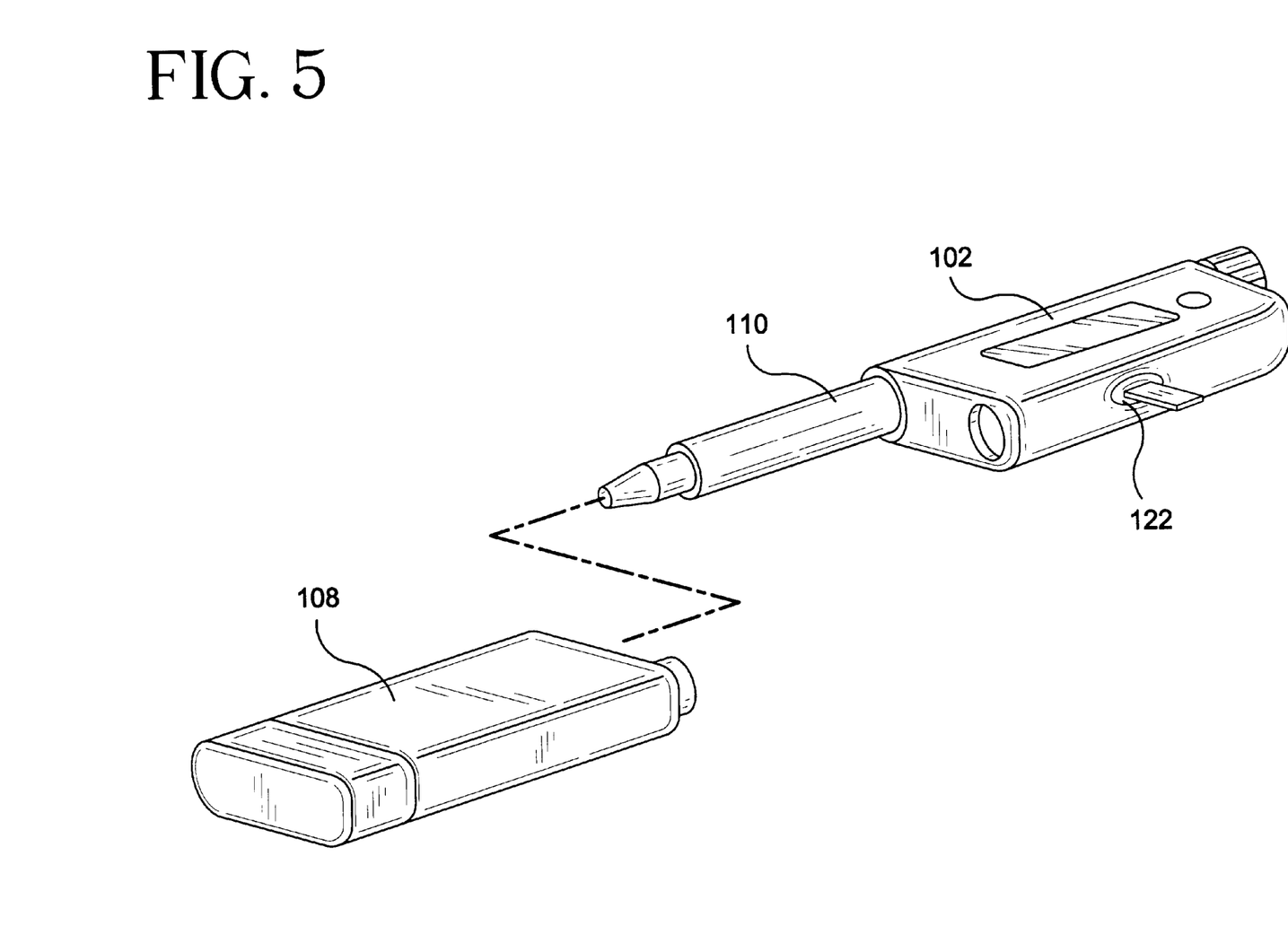
FIG. 5 shows the embodiment of the invention shown in FIG. 4 with the lancer removed from the housing.
Figure 6:
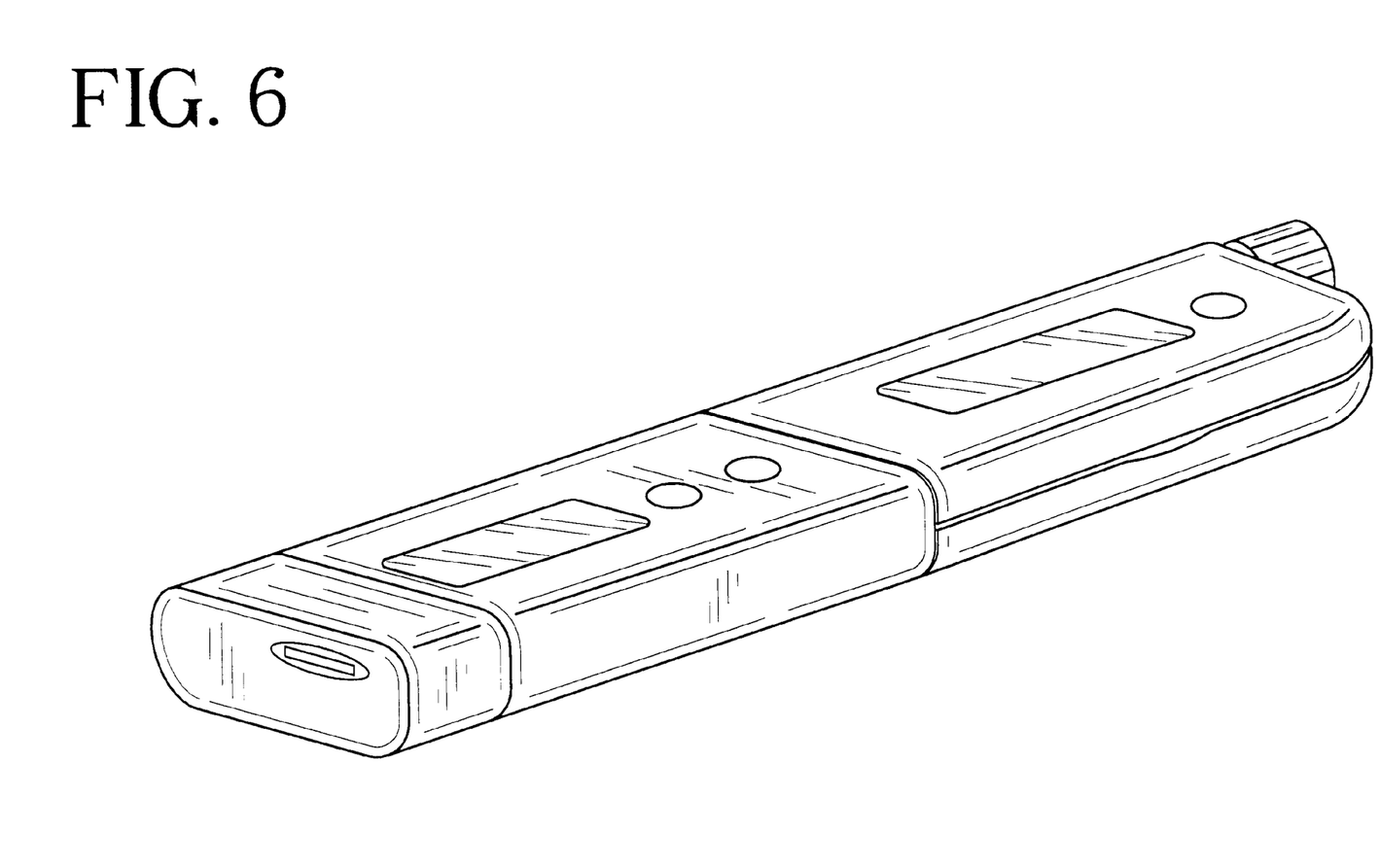
FIG. 6 shows an alternative embodiment of the invention in which the lancer and the blood glucose meter are integrated into a single housing.
Figure 7:
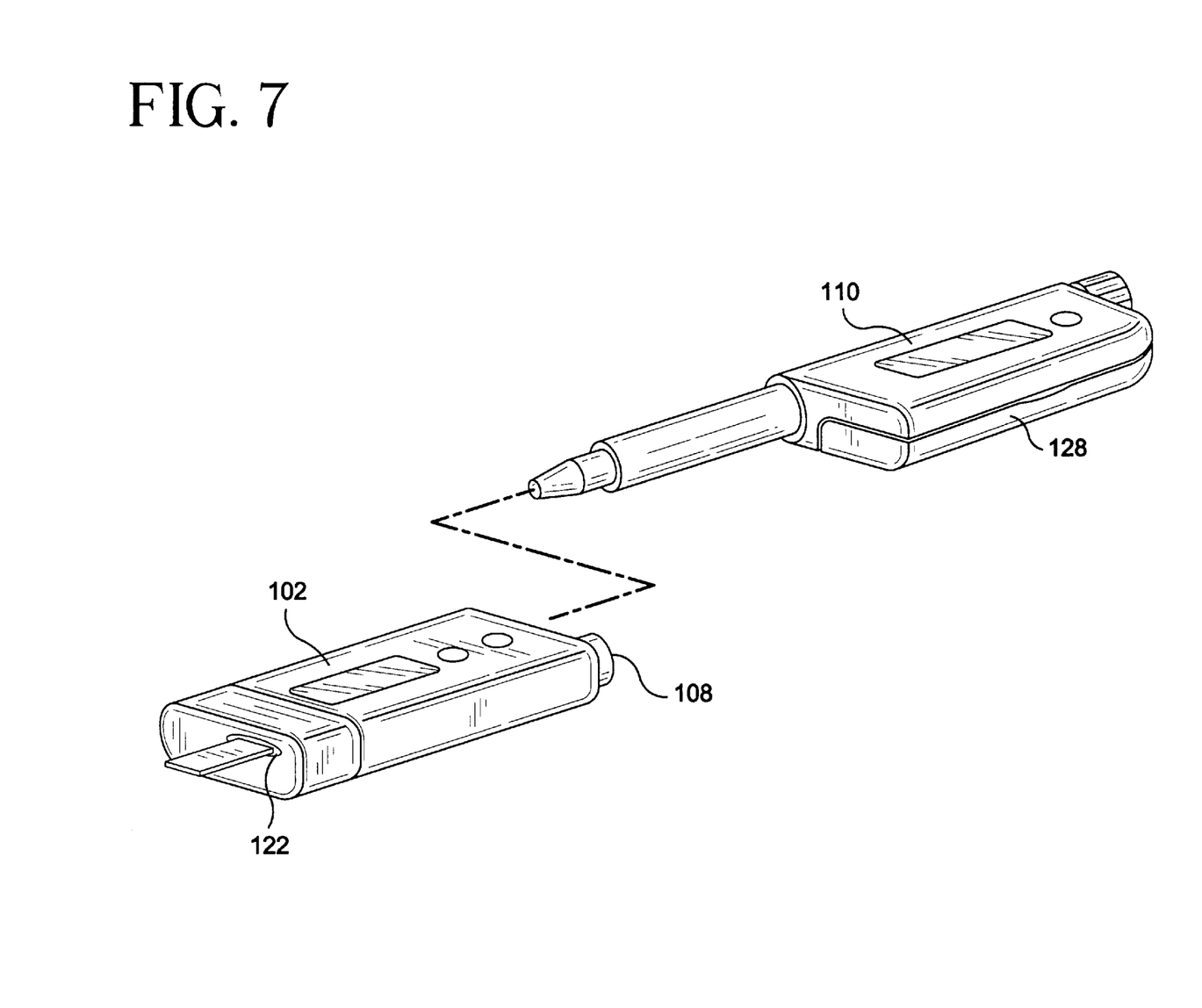
FIG. 7 shows the embodiment of the invention shown in FIG. 6 with the pen removed from the housing.

Although various embodiments are specifically illustrated and described herein, it will be appreciated that modifications and variations of the present invention are covered by the above teachings and are within the purview of the appended claims without departing from the spirit and intended scope of the invention. For example, while the invention has been described in terms of a system for delivering insulin and measuring blood glucose levels, the invention is more generally applicable to the delivery of other chemicals or substances and the monitoring of other bodily fluids for the purpose of diagnosis and/or treatment of disease. In addition, in some embodiments of the invention the medication delivery pen and the lancer both need not be independent and fully detachable from the housing. For example, in some cases, such as shown in FIGS. 4 and 5, both the medication delivery pen and the blood glucose monitor may be integrated into the housing. In other cases, such as shown in FIGS. 6 and 7, both the lancer and the blood glucose monitor may be integrated into the housing. It should be noted that in FIGS. 1–7 like elements are identified by like reference numerals. Yet in other embodiments of the invention the medication delivery pen and lancer may be integrated into the housing while the glucose monitor is either removable, or alternatively, also integrated into the housing.

What is claimed is:

1. In a diagnostic and medication delivery system, a unit comprising:

a housing, said housing having a first compartment adapted to removably receive and store a medication delivery pen and a second compartment adapted to removably receive and store a lancer; and a monitor integrated in the housing for monitoring a characteristic of a sample of a bodily fluid, wherein said monitor is not integrally attached to said medication delivery pen, such that a user is provided with the flexibility to use different medication delivery pens with said system but only one monitor.

2. The unit of claim 1 wherein said first and second compartments are integrally formed with and embedded in said housing.

3. The unit of claim 1 wherein said monitor includes a test strip interface for receiving a test strip on which the fluid sample is located.

4. The unit of claim 1 further comprising at least one data port disposed on the housing for transferring information to and receiving information from an external device.

5. The unit of claim 4 wherein said data port is coupled to the monitor for receiving and downloading the monitored characteristics of the fluid.

6. The unit of claim 5 wherein said data port additionally receives and downloads information from an electronic medication delivery pen disposed in the first compartment.

7. The unit of claim 1 wherein said monitor includes a display located on an inner surface of the second compartment that is exposed when the lancer is not disposed therein and is protected when the lancer is disposed therein.

8. The unit of claim 1 wherein said housing further includes a third compartment adapted to store ancillary items including test strips.

9. The unit of claim 1 wherein said housing further includes a third compartment adapted to store ancillary items including a desiccant.

10. The unit of claim 9 wherein said third compartment includes a cover for securing the ancillary items therein.

11. The unit of claim 8 wherein said third compartment is partitioned into at least two sub-compartments for respectively storing new and used ancillary items.

12. The unit of claim 1 wherein said housing has first and second opposing ends and said first and second compartments are located proximate to different ones of the first and second ends.

13. The unit of claim 12 wherein said monitor includes a test strip interface for receiving a test strip on which the fluid sample is located, said test strip interface being located on the end of the housing proximate to the second compartment.

14. The unit of claim 1 wherein said monitor includes a display and user input operable in a first mode when the pen is stored in the first compartment and in a second mode when the pen is removed from the first compartment, said first mode displaying a blood glucose level and said second mode displaying an insulin dosage level input by a user.

15. The unit of claim 12 wherein the monitor includes a test strip interface for receiving a test strip on which the fluid sample is located, and wherein said test strip interface is also located in the second compartment.

16. The unit of claim 1 further comprising a lancer integrally formed with the second compartment so that the housing, the monitor, and the lancer form a single operable unit.

17. The unit of claim 1 further comprising a medication delivery pen integrally formed with the first compartment so that the housing, the monitor, and the medication delivery pen form a single operable unit.

18. The unit of claim 16 further comprising a medication delivery pen integrally formed with the first compartment so that the housing, the monitor, the lancer and the medication delivery pen form a single operable unit.

19. The unit of claim 2 wherein the first and second compartments include portions that extend internal to the housing for receiving and protecting a needle of the medication delivery pen and a lancet of the lancer, respectively.

20. The unit of claim 7 wherein the first and second compartments include portions that extend internal to the housing for receiving and protecting a needle of the medication delivery pen and a lancet of the lancer, respectively.

21. A diagnostic and medication delivery system, said system comprising:
   a housing;
   a monitor integrally disposed in the housing for monitoring a characteristic of a sample of a bodily fluid;
   a medication delivery pen removably mounted in said housing; and
   a lancer removably mounted in said housing,
   wherein said monitor is not integrally attached to said medication delivery pen, such that a user is provided with the flexibility to use different medication delivery pens with said system but only one monitor.

22. The system of claim 21 wherein the monitor is integrated into the housing so that the housing and monitor form a single operable unit.

23. The system of claim 21 wherein the monitor is removably mounted to said housing.

24. The system of claim 22 wherein said housing has a first compartment adapted to receive and store the medication delivery pen and a second compartment adapted to receive and store the lancer.

25. The system of claim 22 wherein said first and second compartments are integrally formed with and embedded in said housing.

26. The system of claim 22 wherein said monitor includes a test strip interface for receiving a test strip on which the fluid sample is located.

27. The system of claim 22 further comprising at least one data port disposed on the housing for transferring information to and receiving information from an external device.

28. The system of claim 27 wherein said data port is coupled to the monitor for receiving and downloading the monitored characteristics of the fluid.

29. The system of claim 22 wherein the medication delivery pen is an electronic pen.

30. The system of claim 25 wherein the medication delivery pen is an electronic pen.

31. The system of claim 28 wherein the medication delivery pen is an electronic pen.

32. The system of claim 31 wherein said data port additionally receives and downloads information from the electronic medication delivery pen.

33. The system of claim 24 wherein said monitor includes a display for displaying blood glucose levels.

34. The system of claim 33 wherein said display is located on an inner surface of the second compartment that is exposed when the lancer is not disposed therein.

35. The system of claim 22 wherein said housing further includes a third compartment adapted to store ancillary items including test strips.

36. The system of claim 35 wherein said third compartment includes a cover for securing the ancillary items therein.

37. The system of claim 24 wherein said housing has first and second opposing ends and said first and second compartments are located proximate to different ones of the first and second ends.

38. The system of claim 37 wherein the monitor includes a test strip interface for receiving a test strip on which the fluid sample is located, and wherein said test strip interface is located on the end of the housing proximate to the second compartment.

39. The system of claim 24 wherein at least a display of the monitor is located within the second compartment.

40. The system of claim 39 wherein the monitor includes a test strip interface for receiving a test strip on which the fluid sample is located, and wherein said test strip interface is also located in the second compartment.

41. The system of claim 24 wherein the first and second compartments include portions that extend internal to the housing for receiving and protecting a needle of the medication delivery pen needle and a lancet of the lancer, respectively.

42. The system of claim 22 wherein the medication delivery pen and the monitor are in electrical communication with one another.

43. The system of claim 33 wherein the medication delivery pen and the monitor are in electrical communication with one another and said display further displays information received from the pen.

44. The system of claim 22 wherein the medication delivery pen is a mechanical pen.

45. The system of claim 44 wherein said monitor includes a display and user input operable in a first mode when the pen is stored in the first compartment and in a second mode when the pen is removed from the first compartment, said first mode displaying at least a blood glucose level and said second mode displaying at least an insulin dosage level input by a user.

* * * * *